US00PP23423P3

(12) United States Plant Patent
Champion

(10) Patent No.: US PP23,423 P3
(45) Date of Patent: Feb. 26, 2013

(54) CHINESE DOGWOOD TREE NAMED 'LOSELY'

(50) Latin Name: ***Cornus kousa* var. *chinensis***
Varietal Denomination: Losely

(75) Inventor: Bryan Champion, Perry, OH (US)

(73) Assignee: Herman Losely & Son, Inc., Perry, OH (US)

( * ) Notice: Subject to any disclaimer, the term of this patent is extended or adjusted under 35 U.S.C. 154(b) by 16 days.

(21) Appl. No.: 12/925,104

(22) Filed: Oct. 14, 2010

(65) Prior Publication Data

US 2012/0096612 P1 Apr. 19, 2012

(51) Int. Cl.
*A01H 5/00* (2006.01)

(52) U.S. Cl. ..... Plt./220

(58) Field of Classification Search ..... Plt./220
See application file for complete search history.

*Primary Examiner* — Kent L Bell
(74) *Attorney, Agent, or Firm* — Renner, Otto, Boisselle & Sklar, LLP

(57) ABSTRACT

A Chinese dogwood tree named 'Losely', a rounded shrubby tree distinguished by the new leaf growth turning bright yellow in mid summer.

3 Drawing Sheets

Latin name of the genus and species including the variety denomination of the tree claimed: The tree claimed relates to a new and distinct variety of Chinese dogwood tree, botanically known as *Cornus kousa* var. *chinensis*, and known by the cultivar name 'Losely'.

This new cultivar was selected out of a crop of seedlings originating from uncontrolled pollination, growing in Perry, Ohio. This new cultivar was noted as distinctive because of the bright yellow color on the leaves in mid summer. As summer progresses, the yellow foliage will become flushed with red.

The 'Losely' variety is the only variant of Chinese dogwood tree of which I am aware that displays these foliage characteristics. The following selections of Chinese dogwood trees are offered for comparison: 'Gold Star' (unpatented), with gold variegation, but it develops a yellow central leaf blotch that is present the entire growing season; 'Temple Jewel' (unpatented) has a faint yellow central blotch in the spring, disappearing by summer when the leaves are mature; 'Madison' (U.S. Plant Pat. No. 16,129) has gold foliage with red blotching appearing in summer, coloration not consistent from year to year ranging from almost no color to some color.

The original 'Losely' cultivar was lost in a flood in 2006. Prior to the loss of the parent tree, the 'Losely' cultivar had been asexually reproduced in Perry, Ohio by grafting. The oldest of the 'Losely' cultivar is approximately 6 years old and is approximately 2.4 meters tall and 2 meters wide. Branching starts at approximately 20 cm above ground level. There are 3 main branches. The largest branch is approximately 4 cm in diameter, the next largest is approximately 3 cm in diameter and the smallest is approximately 2.5 cm in diameter.

The 'Losely' cultivar has been asexually reproduced in Perry, Ohio, by means of grafting. All trees propagated by this method have displayed the same unique characteristics of the original tree.

Figure 1:
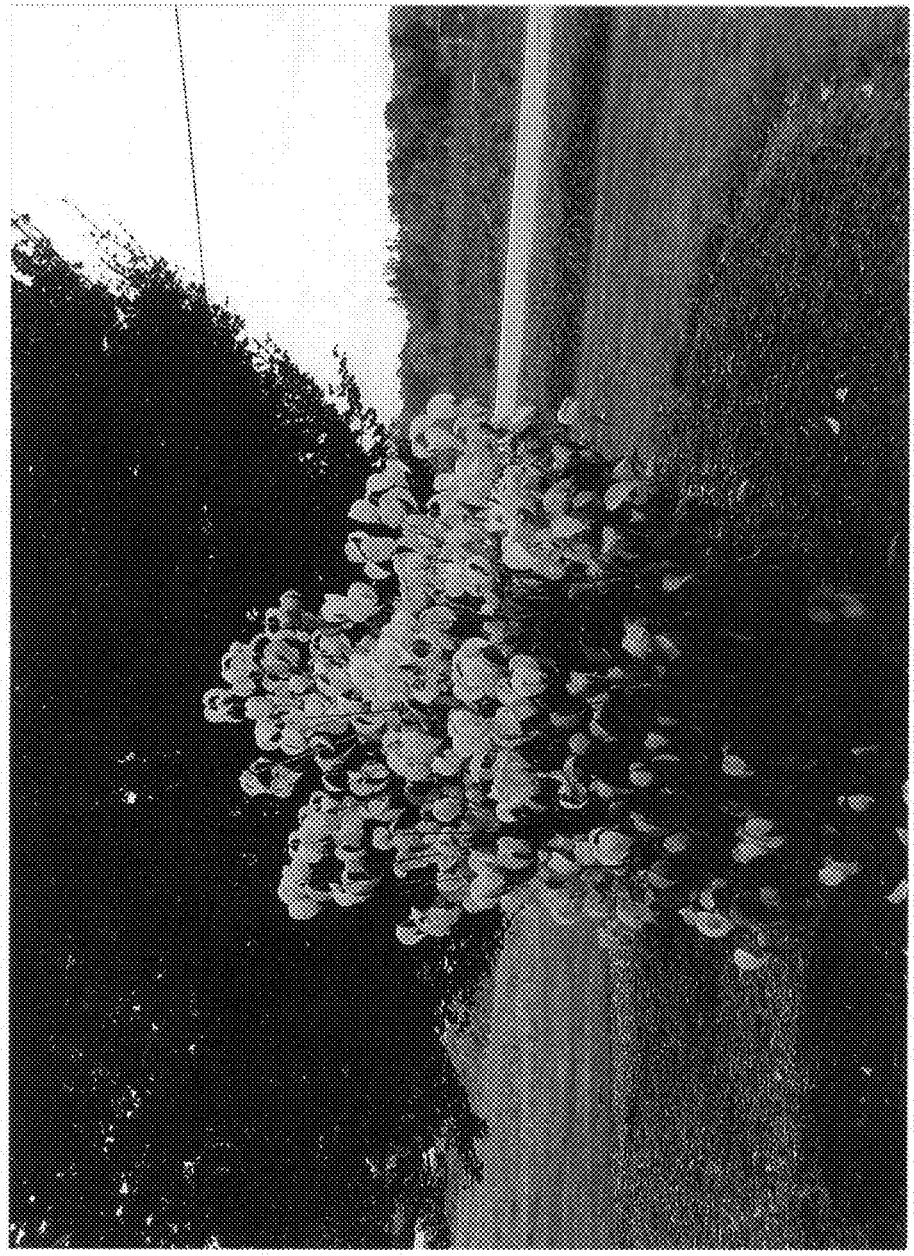
FIG. 1 is a colored photograph illustrating the overall appearance of the 'Losely' cultivar in the summer.
Figure 2:
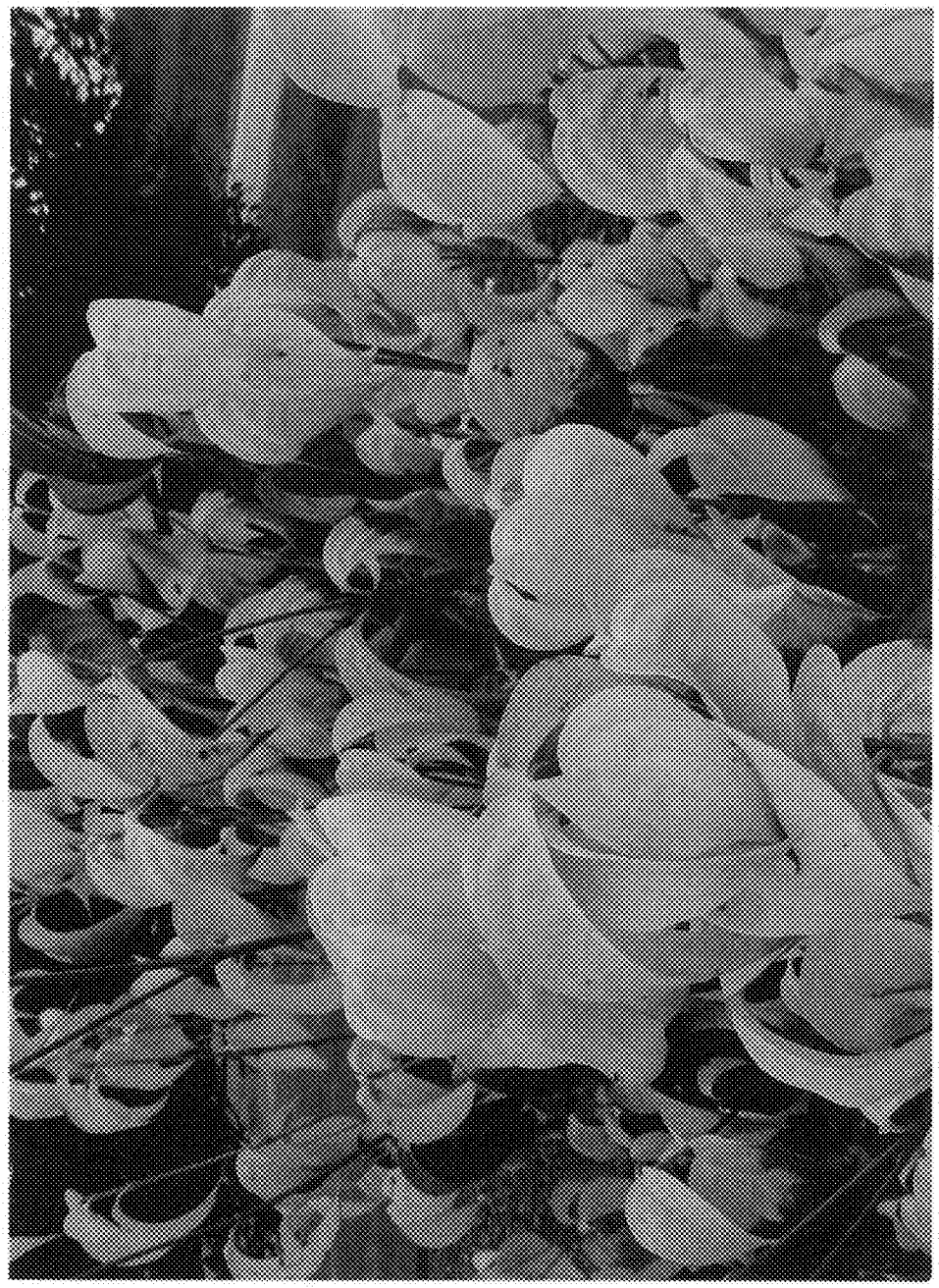
FIG. 2 is a colored photograph illustrating the prolonged yellow coloration on the leaves of 'Losely' in the summer.
Figure 3:
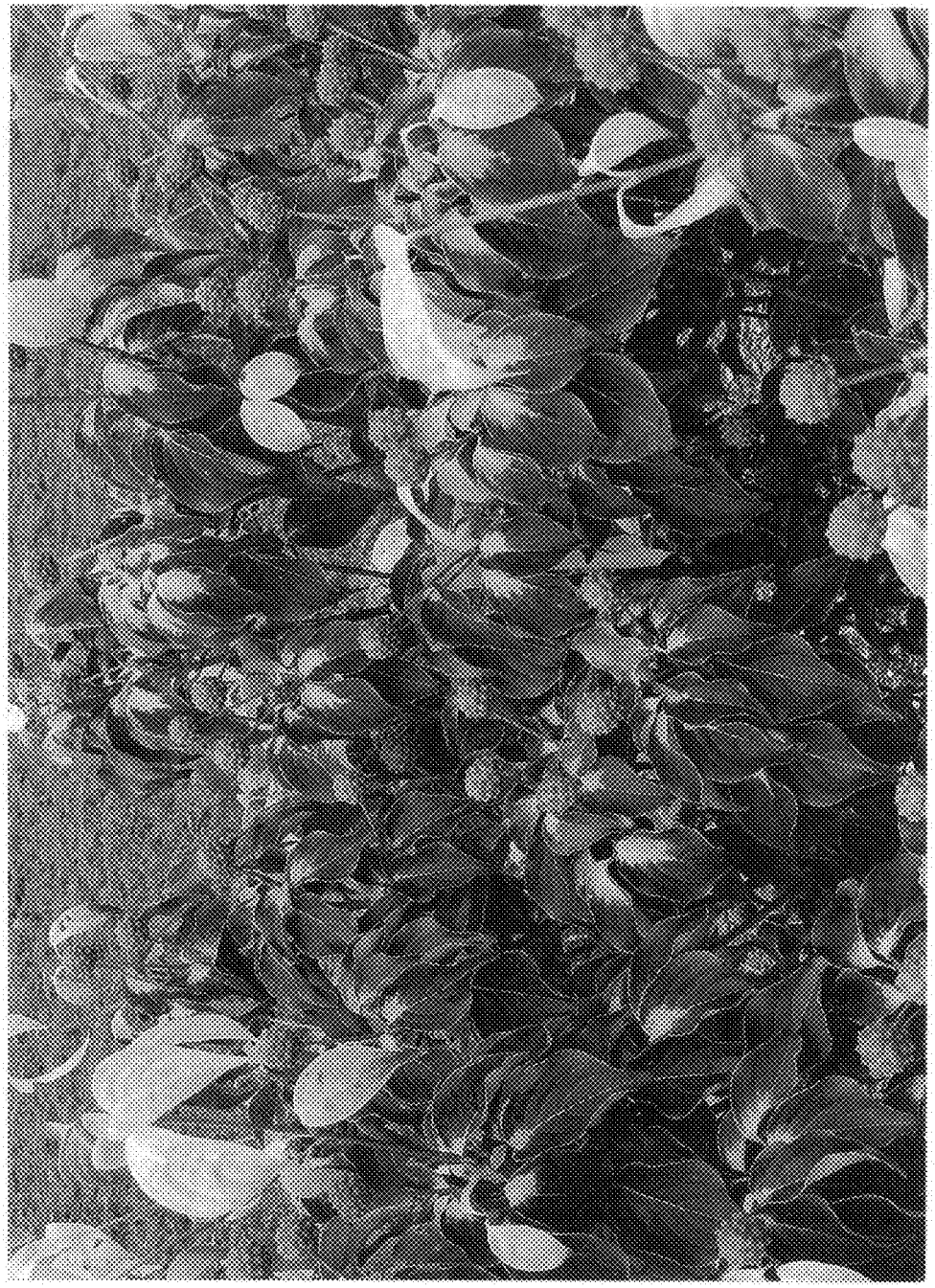
FIG. 3 is a colored photograph illustrating the coloration of the current season's growth found on the inner part of 'Losely' in the summer. This coloration may range from green foliage to leaves with yellow advancing from the leaf petiole and the leaf base down the leaf blade to varying degrees.

All of the drawing figures show the colors as truly as is reasonably possible to obtain in colored reproductions of this type.

The following is a detailed description of the new 'Losely' cultivar. In all cases, where color is different from the typical and is considered a distinguishing feature of this variety, reference is made to specific colors on The R.H.S. Colour Chart (1995 ed.) published by The Royal Horticultural Society, London, England. Here follows a detailed description of the characteristics of this cultivar, as displayed by the 6 year old specimen grown in Perry, Ohio. Coloration of leaves and bark may be variable, due to conditions of nutrition, stress, age of tree, location on tree and the presence/absence of sun/shade. Tree part comparisons have been made from a mature tree where growth rates and characteristics are considered typical.

BOTANICAL DESCRIPTION

Parentage: Unknown—selected out of a crop of seedlings originating from uncontrolled pollination, growing in Perry, Ohio.

Hardiness: Hardy in USDA Hardiness Zone 4b (−25 degree F.)

Growth rate: Moderate, more rapid in youth.

Form/size: A shrubby tree 6-10 meters in height and spread at maturity. Rounded as a young tree, maintaining that shape, with a layered, horizontal branching habit. A wide range of factors, especially location, age and if the tree is multi-stem or single stem, influences sizes of stems and branches. It is not possible to make a predictable correlation between the diameter of a primary stem and any branch arising from it.

Stems: Young stems initially slender, glabrous grey green (Greyed-Green Group 194C) with whitish (Greyed-White Group 156C) lenticels present on all bark areas diminishing somewhat on more mature surfaces to orange (Orange-White Group 159A). Typical and observed lenticel height is 1 mm×0.5 mm diameter—45 to 68 lenticels per square centimeter. Slightly textured, smooth bark on the lower trunk 15.25 cm from the ground is of the color grey green (Greyed-Green 197A). Trunk diameter is 4 cm at 15.25 cm.

Branches: New shoots green (Yellow-Green Group 144C) turning to grey orange (Greyed-Orange 177A) over time. One and two year old twigs are grey orange (Greyed-Orange Group 165A). The final 2.5-10 cm of the twig, exclusive of terminal buds may be flushed red-purple (Red-Purple Group 58A) on the upper side of branch and green (Green Group 143C) on the lower side. Mature branch color is (Greyed-Green Group 197A).

Leaves: Deciduous, simple entire leaf, elliptic-ovate with acuminate tips and cuneate bases, 5-12 cm long and 3.5-7.5 cm wide. Leaf petioles are 5-10 mm long by 2 mm in diameter on average and of the color (Yellow-Green 144D). Leaf blades glabrous on top, glabrous underneath, lacking tufts of hairs in leaf vein axils on underside of leaf. Newly emerging leaves in the spring exhibit yellow green (Yellow-Green Group 144B) on upper side of leaves and (Yellow-Green Group 144C) underneath, darkening to green (Green Group 139A) on upper side of leaves and (Green Group 139B) below. Many leaves of the current year's growth flush become yellow (Yellow Group 13B) by midsummer. The yellow coloration is exhibited from leaf petiole and base down leaf blade and may include from ⅓ to entire leaf. Coloration begins in July in Perry, Ohio (41.81 degrees North Latitude by 81.13 degrees West Longitude). Overall, current season's growth found on the inner part of the tree may range from green foliage to leaves with yellow advancing down the leaves to varying degrees. The more vigorous new growth found on the outside canopy exhibits mainly solid yellow leaves. At maturity, yellow leaves develop red blushes (Red Group 46B) with the yellow predominating. Much later, these blushed yellow leaves become infused with more red (Red Group 46B and 46C) and orange (Red Group 42B and 42C) fall colors. Leaves that have remained green will later exhibit red (Red Group 46B and 46C) and orange (red Group 42B and 42C) fall colors typical of the species. The yellow coloration of the foliage appears year after year regardless of weather conditions.

Buds: Buds are two types—Globose, tapering flower buds averaging 7 mm in length by 5 mm in width at base, color gray-brown (Gray-Brown Group 199A) and sharply tapered vegetative buds averaging 4 mm in length by 2 mm in width at base, color brown (Brown Group 200B).

Flowers: Inconspicuous greenish yellow true flowers sessile in compact umbels are surrounded by a showy white involucre much exceeding the flowers. The true flowers are (Green Group 143C) at petal tip and (Yellow-Green Group 15D) at petal base on the lower surfaces and (Green-White Group 157C) on upper surfaces. The rounded, central umbel approximately 1 cm wide×1 cm high at the top of a peduncle 5-6 cm in length and greenish (Yellow-Green Group 144C). The valvate—4 petaled flowers consist of four stamens (Green-White Group 157C) with filament (Green-White Group 157C) length 2 mm×0.5 mm wide. The anther, initially translucent 0.75 mm-1 mm long by 0.5 mm wide, maturing to brown (Brown Group 200A). One columnar pistil per flower with ovary color (Greyed-Purple Group 187A). The style is of (Greyed-Purple Group187A) 1 mm×0.5 mm wide. The stigma is flat, greenish-yellow (Yellow-Green Group 150D) at first, maturing to (Greyed-Purple 187A) and 0.5 mm in width. The number of inconspicuous flowers will vary per umbel and do not all open at the same time—opening from outside in. The involucre of four partially overlapping smooth, entire, oval-acuminate creamy white bracts form a 4-pointed symmetrical star characterizing each individual inflorescence. Initially, bracts with rounded base and acuminate apices are white (White Group 155C) on upper side and (White Group 157D) underneath. Mature bracts resemble (Green-White Group 157A) above, (Green White Group 157D) below. Typical and observed bract size averages 4.5-5 cm long and 3.5-4 cm wide, thereby producing an inflorescence with an overall width of 9-10.5 cm. Flowering commences last week of May to first week of June in Perry, Ohio lasting about six weeks. Flowers of this cultivar are borne more on the inside of the tree and are not overly abundant.

Fruits: The fruits connate into a globular fleshy head; predominately red (Red Group 46C) and approximately 3 cm in diameter at maturity. The syncarp is initially held upright on a 5-6 cm peduncle, later becoming pendulous.

Pests, diseases: May be susceptible to Powdery Mildew, Borer (Dogwood).

I claim:

1. A Chinese dogwood tree named 'Losely', as described and illustrated, a shrubby tree distinguished by the bright yellow coloration on the leaves in mid summer.

* * * * *